United States Patent [19]

Wheeler et al.

[11] Patent Number: 5,120,844
[45] Date of Patent: Jun. 9, 1992

[54] SUBSTITUTED TRIAZINES

[75] Inventors: Edward L. Wheeler, Watertown; Franklin H. Barrows, Naugatuck; Robert J. Franko, Beacon Falls, all of Conn.

[73] Assignee: Uniroyal Chemical Company, Inc., Middlebury, Conn.

[21] Appl. No.: 555,206

[22] Filed: Jul. 19, 1990

Related U.S. Application Data

[62] Division of Ser. No. 247,219, Sep. 21, 1988, Pat. No. 4,972,010.

[51] Int. Cl.⁵ .................. C07D 251/18; C07D 251/70; C07D 403/12; C07D 413/12
[52] U.S. Cl. ......................... 544/209; 544/211; 544/212; 544/197; 544/198; 544/208; 544/206; 544/207
[58] Field of Search ............... 544/211, 212, 197, 198, 544/208, 209, 206, 207

[56] References Cited

U.S. PATENT DOCUMENTS

| | | | |
|---|---|---|---|
| Re. 19,654 | 7/1935 | Reed | 524/100 |
| 2,909,421 | 10/1959 | Gysin | 544/197 |
| 3,156,690 | 11/1964 | Dexter et al. | 544/197 |
| 3,179,718 | 4/1965 | Wei et al. | 260/889 |
| 3,202,681 | 8/1965 | Dexter et al. | 524/100 |
| 3,205,193 | 9/1965 | Dexter et al. | 524/100 |
| 3,255,191 | 6/1966 | Dexter et al. | 524/100 |
| 3,257,354 | 6/1966 | Dexter et al. | 544/197 |
| 3,350,449 | 10/1967 | Wheeler et al. | 260/576 |
| 3,414,570 | 12/1968 | Coburn | 544/197 |
| 3,419,639 | 4/1968 | Gentile | 260/889 |
| 3,630,974 | 12/1972 | Ladocsi et al. | 260/889 |
| 3,706,819 | 12/1972 | Usamoto et al. | 260/889 |
| 3,828,002 | 8/1974 | Westlinning | 524/100 |
| 3,830,274 | 8/1974 | Waser, Jr. | 152/355 |
| 3,915,907 | 10/1975 | Hopper | 260/5 |
| 3,937,862 | 2/1976 | Dillenschneider | 428/409 |
| 4,003,420 | 1/1977 | Sandstrom et al. | 152/355 |
| 4,479,008 | 10/1984 | Batorewicz et al. | 564/410 |
| 4,617,390 | 10/1986 | Hoppe et al. | 544/197 |
| 4,650,867 | 3/1987 | Ronco et al. | 544/197 |
| 4,786,672 | 11/1988 | Wehner | 524/100 |

FOREIGN PATENT DOCUMENTS

| | | | |
|---|---|---|---|
| 8105752 | 7/1982 | Netherlands | 524/100 |
| 922040 | 3/1963 | United Kingdom | 524/100 |

OTHER PUBLICATIONS

Chem. Abs., vol. 105, No. 10, (Sep. 8, 1986), p. 74, Abstract No. 80387f, Nakamura.

*Primary Examiner*—John M. Ford
*Attorney, Agent, or Firm*—Raymond D. Thompson

[57] ABSTRACT

Disclosed are tris-substituted 1,3,5-triazine compounds having at least one (N-alkyl-p-phenylendediamino) group on the triazine ring. The preferred compositions are tri-substituted with the alkyl p-phenylenediamino group. The preferred compounds may be prepared by reacting N-alkylphenylenediamine with a cyanuric halide.

4 Claims, No Drawings

SUBSTITUTED TRIAZINES

This is a division of application Ser. No. 247,219, filed Sep. 21, 1988, now U.S. Pat. No. 4,972,010.

BACKGROUND OF THE INVENTION

This invention relates to new triazine compounds which are useful as antiozonants for rubber, processes for their manufacture, and to their use in inhibiting the deteriorating effect of ozone on unsaturated polymers.

It is well known that ozone causes surface cracking of conventional highly unsaturated rubber vulcanizates when the rubber is placed under strain in an ozone environment. The most severe deterioration occurs when a small number of cracks are formed which grow rapidly into deep, disruptive fissures. These ozone cracks seriously shorten the serviceable life of the article.

Chemical antiozonants have been developed which retard the formation of the ozone cracks occurring under static and dynamic conditions. Examples of antiozonants in common use include: N-phenyl-N'-(1,3-dimethylbutyl)-p-phenylenediamine; N-phenyl-N'-isopropyl-p-phenylenediamine; N-phenyl-N'-(1,4-dimethylphentyl)-p-phenylenediamine; N-phenyl-N'-(1-methylheptyl)-p-phenylenediamine; N-phenyl-N'-cyclohexyl-p-phenylenediamine; mixed diaryl-p-phenylenediamines; N,N'-diphenyl-p-phenylenediamine; N,N'-di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonyl-p-phenylenediamine and blends of these materials.

The use of these well known paraphenylenediamine materials has improved ozone protection under both static and dynamic conditions, however, even the best of the class just described have a very strong tendency to both stain and discolor. The term "stain" or "staining" is herein used to described the characteristic of a material to diffuse through a polymeric substrate and discolor the adjacent surface. This diffusion staining is highly objectionable in most light colored rubber articles. In tires, which is the largest application in which the ozone protection is required, the tendency to diffusion staining of the aforementioned paraphenylenediamine materials is objectionable particularly in white sidewall type tires. Even in non-white sidewall type tires, the tendency of the materials to diffuse to the surface of the tire sidewall can be objectionable in that a brown, dull surface is created on the tire sidewall. This is aesthetically objectionable in that it detracts from the general jet black, smooth appearance of a new tire. It is obvious that in a white sidewall tire, the migration of the brown discoloring material to the surface of the white sidewall is highly objectionable and generally difficult to remove during cleaning of the tire surface.

Waxes have been long utilized to inhibit ozone cracking in articles under stress in static condition by incorporating the wax into the rubber compound prior to vulcanization. The wax functions by migrating to the surface of the rubber article to form a film which acts as a physical barrier to the ozone attack. However, during dynamic flexing in service, the wax film is cracked or disrupted and the tendency is for the article to exhibit fewer and more severe ozone cracks than if no wax had been incorporated. Therefore, for many service conditions, the use of wax is impractical due to the dynamic conditions under which the article is expected to perform.

An object of this invention is to provide an antiozonant material which is highly effective in protecting a highly unsaturated polymer substrate from ozone attack. A further object is to provide ozone protection in a static condition at very low levels and to protect the rubber article during extended aging conditions against ozone attack. Yet another object is to produce a compound which does slowly diffuse and does not produce an objectionable brown bloom.

The novel substituted triazine compounds of the invention have provided exceptional long term ozone protection under static conditions with and without using wax. An advantage of the substituted triazine compounds is that it produces a substantially non-staining antiozonant of high molecular weight. A further advantage is that it slowly blooms to the surface of the rubber article. A further advantage is that the triazine compounds of the invention provide outstanding dynamic protection without the use of waxes preferably by blending said triazine compounds with other known antiozonants and antioxidants. Another advantage is that the compounds do not tend to increase scorchiness of the compounded rubber stock in which it is used. This improves processing safety over other paraphenylenediamine antiozonants.

BRIEF DESCRIPTION OF THE INVENTION

The object and advantages of this invention may be obtained using a compound of the general formula:

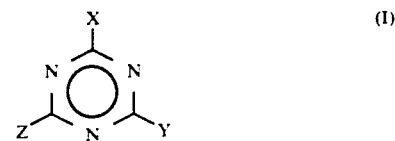

in which
X is

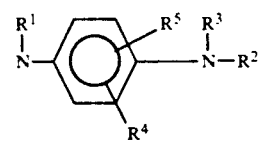

$R^1$ is hydrogen, $C_1$-$C_{11}$ linear or branched alkyl, $C_3$-$C_6$ cycloalkyl, phenyl or phenyl substituted with $C_1$-$C_4$ alkyl;
$R^2$ is $C_1$-$C_{11}$ alkyl, $C_3$-$C_6$ cycloalkyl,

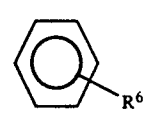

or
$R^2$ is

when $R^3$ is H;

$R^3$ is hydrogen, phenyl or $C_1-C_{11}$ linear or branched alkyl;

$R^4$ is hydrogen or $C_1-C_8$ linear or branched alkyl;

$R^5$ is hydrogen or $C_1-C_8$ linear or branched alkyl;

$R^6$ is $C_1-C_8$ linear or branched alkyl or $C_1-C_{12}$ alkoxy, hydrogen when $R^1$ is $C_1-C_{11}$ linear or branched alkyl or $C_1-C_8$ linear or branched alkyl when $R^1$ is hydrogen;

$R^7$ is $C_1-C_{12}$ linear or branched alkyl;

Y is X, hydrogen, $C_1-C_4$ alkyl, —SH, $SR^8$, —OH, —$OR^8$,

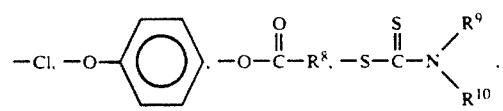

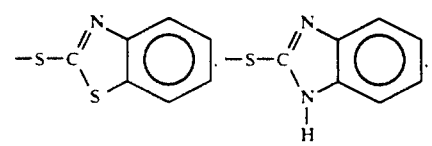

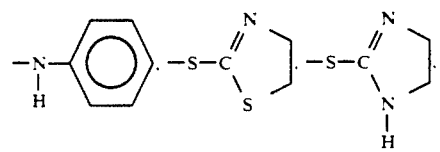

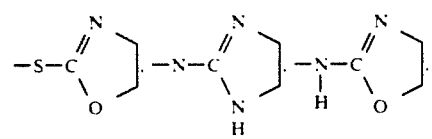

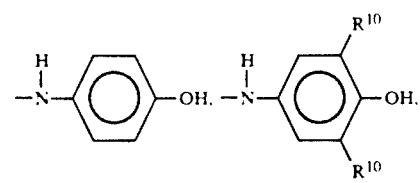

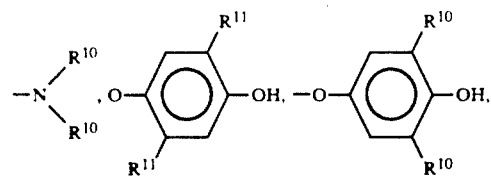

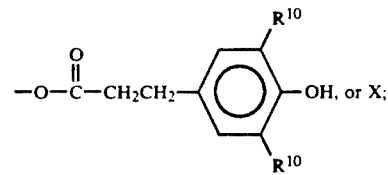

$R^8$ is $C_1-C_{12}$ linear or branched alkyl, $R^9$ is $C_1-C_5$ linear or branched alkyl, $R^{10}$ is $C_1-C_5$ linear or branched alkyl, $R^{11}$ is hydrogen, $C_3-C_{16}$ linear or branched alkyl, Z is X or Y or

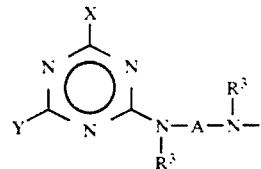

or

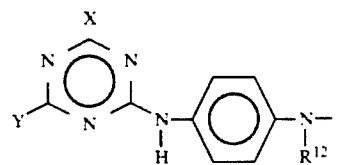

A is $C_2-C_{10}$ linear alkylene $C_5-C_{10}$ cycloalkylene, phenylene or $C_7-C_9$ arylalkylene;

$R^{12}$ is hydrogen or $C_3-C_{11}$ alkyl;

when Y is not the same as X, then $R_6$ can be hydrogen; when Z is the same as Y, then Y may not be —$SR^8$, —OH, —$OR^8$,

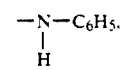

—O—$C_6H_5$.

The novel compounds of the present invention may be prepared by a process comprising:

reacting a phenylenediamine with a triazine in a solvent to form a reaction mixture including a (diamino)-1-3,5-triazine trihydrohalide; and neutralizing said (diamino)-1-3,5-triazine trihydrohalide with a base to form a triazine.

Unsaturated polymers may be stabilized against ozone degradation by incorporation therein of an effective amount the novel compounds of structure (I).

Unsaturated polymer-containing rubber article may be stabilized against ozone degradation by incorporation therein of an effective amount the novel compounds of structure (I).

DETAILED DESCRIPTION OF THE INVENTION

Referring to structure (I), set forth above, preferred compounds are those in which Y and Z are the same as X. That is, a substituted paraphenylenediamino radical substituted on the triazine ring. The more preferred compositions are those in which the $R^2$ group on the X, Y and Z groups are linear or branched $C_3-C_{18}$ alkyl groups. The alkyl groups preferred are those with a secondary carbon in the alpha position to the nitrogen. In this configuration, the antiozonant activity of the compound is believed to be enhanced. Therefore, the more preferred alkyl groups are branched chains which provide an alkyl substituent which is in accordance with this configuration. The cycloalkyl or $C_1-C_{12}$ alkyl substituted cycloalkyls provide such a alpha carbon configuration as well. The structure of formula I which is most preferred at this time are compounds in which $R^2$ is a $C_6-C_8$ branched chain alkyl group.

General nomenclature for Y, when Z is the same as X is that Y may be X; hydrogen; lower alkyl; thiol; thioalkyl; hydroxy; alkoxy; chloro; phenoxy; acyl; N-N'dialkyldithiocarbamyl; benzothiazolylthio; benzimidazolylthio; anilino; thiazolidylthio; imidazolidylthio; oxazolidylthio; imidazolidylamino; oxazolidylamino; 4 hydroxyanilino; 3,5 dialkyl-4 hydroxyanilino; dialkylamino; 2,5 dialkyl, 4 hydroxyphenoxy; 3,5 dialkylhydroxyphenoxy; and 3,5 dialkylhydroxyphenylpropionyl. Similarly, when Z is the same as Y then Y may be $X$, or hydrogen; lower alkyl; thiol; chloro; acyl; dialkyldithiocarbamyl; benzimidazolylthio; benzothiazolylthio; thiazolidylthio; imidazolidylthio; oxazolidylthio; imidazolidylamino; oxazolidylamino; 4-hydroxyanilino; 3,5-dialkyl-4-hydroxyanilino; 3,5-dialkylhydroxyphenoxy or 3,5 dialkyl-4-hydroxy phenylpropionyl. However, Y may not be $-SR^8$, $-OH$, $OR^8$, $N-C_6H_5$ or $-O-C_6H_5$ when Z and Y are the same. H.

Examples of some preferred chemicals of the present invention are: 2,4,6-tris(N-1,4-dimethylpentyl-p-phenylenediamino)-1,3,5-triazine; 2,4,6-tris(N-isopropyl-p-phenylenediamino)-1,3,5-triazine; 2,4,6-tris (N-cyclohexyl-p-phenylenediamino)-1,3,5-triazine; 2,4,6-tris (N-sec-butyl-p-phenylenediamino)-1,3,5-triazine; 2,4,6-tris (N-1,3-dimethylbutyl-p-phenylenediamino)-1,3,5-triazine; 2,4,6-tris(N-1-methylheptyl-p-phenylenediamino)-1,3,5-triazine; 2,4,6-tris(N-2,4-di-tert-butylcyclohexyl-p-phenylenediamino)-1,3,5-triazine; 2,4,6-tris(N-2-sec-butylcyclohexyl-p-phenylenediamino)-1,3,5-triazine, 2,4,6-tris(1-methyldecyl-p-phenylenediamine)-1,3,5-triazine; 2,4,6-tris(N-1,4-dimethylpentyl-2-methyl-p-phenylenediamino)-1,3,5-triazine; 2,4,6-tris(N-1,4-dimethylpentyl-2-ethyl-p-phenylenediamino)-1,3,5-triazine; 2,4,6-tris(N-isopropyl-2-ethyl-p-phenylenediamino)-1,3,5-triazine; 2,4,6-tris(N-isopropyl-2-methyl-p-phenylenediamino)-1,3,5-triazine; 2,4,6-tris[N,N'-bis(isopropyl)-p-phenylenediamino]-1,3,5-triazine; 2,4,6-tris[N,N-bis(1,4-dimethylpentyl)-p-phenylenediamino]-1,3,5-triazine; 2,4,6-tris(N'-2-isopropylphenyl-p-phenylenediamino)-1,3,5-triazine; 2-(N-1,4-dimethylpentyl-p-phenylenediamino)-4,6-bismercapto-1,3,5-triazine; 1,6-bis[2-imino-4,6-bis(N-1,4-dimethylpentyl-p-phenylenediamino)-1,3,5-triazino]hexane; 1,6-bis[2-imino-4,6-bis(N-phenyl-p-phenylenediamino)-1,3,5-triazino]hexane; N,N'-bis[4,6-bis(N-1,4 dimethylpentyl-p-phenylenediamino-1,3,5-triazinyl-2)]p-phenylenediamine; N-1,4-dimethylpentyl-N,N'-bis[4,6-bis(N-1,4-dimethylpentyl-p-phenylenediamino-1,3,5-triazinyl-2)]p-phenylenediamine.

The compounds of the invention can be synthesized advantageously by the following general method. Although the reagents may be added in different order as shown in some of the examples, the preferred method is as follows:

The substituted -p-phenylenediamine, which is prepared by methods known to those familiar with the art, is reacted with 2,4,6-tri-halogeno-1,3,5-triazine. A molar equivalent of the preferred tri-halo triazine commonly called cyanuric chloride is added as a powder to a solution of three plus moles of the -p-phenylenediamine in a suitable solvent such as isopropanol, at ambient temperatures with appropriate cooling. The first two halogen atoms are displaced rapidly. The reaction mixture is then heated to 60°-80° C. in order to complete the displacement of the third halogen atom. After 4-5 hours heating at 60°-80° C. the formation of the 2,4,6-tris-(substituted-p-phenylenediamino)-1,3,5-triazine trihydrochloride is complete.

The process is unique in that the basicity of the substituted phenylenediamine allows the displaced halogen atom of the cyanuric halide to form the hydrohalide directly thereby enabling isolation of the trihalide and effecting a purification step.

The tris-hydrochloride may be removed by filtration, then reslurried in a suitable water miscible solvent, neutralized with aqueous base such as sodium hydroxide, and crystallized from the aqueous solvent mixture.

If the starting substituted -p-phenylenediamine is sufficiently pure, or a less pure product is acceptable, isolation of the tris-hydrochloride is not necessary, and the reaction mixture can be neutralized and the product crystallized and isolated by filtration.

Temperature control of the reaction is of some importance. It is preferred that the first stage of the reaction take place below 30° C. and that the second stage take place at least 30° C. above the first stage. Selection of the optimal temperatures are, of course, dependent upon the identity of the p-phenylenediamine and solvent which is chosen.

Preferred solvents are alcohols although any suitable solvent may be utilized. The term solvent is meant to include an excess of the substituted -p-phenylenediamine which may serve to solvate the reaction product and allow subsequent isolation.

It is noted here that any use of the term "alkyl", in the context of a starting material (i.e., N-alkyl-p-phenylenediamine) or the final substituted triazine compounds of this invention, is deemed to include cycloalkyl and alkyl substituted cycloalkyl structures as well.

When the substituents on the triazine ring are not identical, the cyanuric chloride is first reacted with the desired paraphenylenediamine followed by reaction with the compounds containing structures set forth above as useful for Y.

The compounds of the invention are most advantageously utilized as antiozonants to protect highly unsaturated polymers such as natural or synthetic elastomers. Representative of the highly unsaturated polymers which may be employed in the practice of this invention are diene elastomers. Such elastomers will typically possess an iodine number of between about 100 and about 250, although highly unsaturated rubbers having a higher or a lower (i.e., of 50-100) iodine number may also be employed. Illustrative of the diene elastomers which may be utilized are polymers based on conjugated dienes such as 1,3-butadiene; 2-methyl-1,3-butadiene; 1,3-pentadiene; 2,3-dimethyl-1,3-butadiene; and the like, as well as copolymers of such conjugated dienes with monomers such as styrene, alpha-methylstyrene, acrylonitrile, methacrylonitrile, methyl acrylate, ethyl acrylate, methyl methacrylate, ethyl methacrylate, vinyl acetate and the like. Preferred highly unsaturated rubbers include natural rubber, cis-polyisoprene, polybutadiene, poly(styrene-butadiene), polychloroprene and poly(acrylonitrile-butadiene). Moreover, mixtures of two or more highly unsaturated rubbers may be employed. Also, mixtures of the highly unsaturated rubbers with elastomers having lesser unsaturation such as EPDM, EPR, butyl or halogenated butyl rubbers are also within the contemplation of the invention.

The novel compounds of the invention may be used in combination with other antiozonants and less preferably with microcrystalline waxes as are commonly used to protect against static ozone attack. The other antiozonants which may be utilized include any of the commonly recognized paraphenylenediamine class of materials: N-phenyl-N'-(1,3-dimethylbutyl)-p-phenylenediamine; N-phenyl-N'-isopropyl-p-phenylenediamine; N-phenyl-N'-(1-methylhepthyl)-p-phenylenediamine; N- phenyl-N'-cyclohexyl-p-phenylenediamine; mixed diaryl-p-phenylenediamines; N,N'-diphenyl-p-phenylenediamine; N,N'-di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonyl-p-phenylenediamine; N-phenyl-N'-alkyl-p-phenylenediamine; 6-ethoxy-1,2-dihydro-2,2,4-trimethylquinoline; and nickel dibutyl dithiocarbamate.

A most preferred antiozonant to be use in combination with the novel triazine compounds of the invention is N-phenyl-N'-(1,3-dimethylbutyl)-p-phenylenediamine.

The highly unsaturated polymers to be protected may be formulated in conventional manner with the many usual compounding ingredients, for example, vulcanizing agents, accelerators, activators, retarders, antiozonants, antioxidants, plasticizing oils and softeners, fillers, reinforcing pigments and carbon blacks.

The novel compounds of the invention may be added to an unsaturated polymer at a level of from 0.1 to about 10 parts by weight per hundred parts by weight of rubber hydrocarbon (hereinafter PHR). For these purposes the polymer is assumed to be a natural or synthetic rubber. A more preferred addition level is about 1 to about 6 parts PHR. The most preferred level is from about 2 to about 4 parts PHR. When the triazine compounds of the invention are used in combination with other antiozonants such as the paraphenylenediamine class of materials, they may be added in a blend which totals to the ranges set forth above. The compounds of the invention may be blended with the other antiozonants at ratios ranging from 1:3 to 3:1. More preferred is a ratio range of 2:3 to 3:2. These ratios are meant to indicate the percentages are 40:60 to 60:40 where in all cases the triazine compounds of the invention are the first number of each ratio. It should be noted that in certain applications and with certain other antiozonants, the PHR ranges of antiozonant listed above may be varied in order to obtain the optimal protection. Reasonable experimentation must be undertaken in order to optimize the ratios and overall levels of the blend when the triazine compounds of the invention are blended with other conventional antioxidants and antiozonants.

The novel triazine compounds of the invention may be synthesized by a suitable synthesis route. The following synthesis examples are provided to illustrate a currently preferred method of manufacturing certain of the class of triazine compounds of the invention.

SYNTHESIS EXAMPLES

Example 1:
2,4,6-Tris(N-1,4-Dimethylpentyl-P-Phenylene Diamino)-1,3,5-Triazine In a 3-liter, four-necked, round-bottomed flask equipped with a thermometer, a mechanical stirrer, a condenser, and a dropping funnel was placed 1500 ml of isopropanol. The isopropanol was cooled to $-10°$ C. and 184.4 grams (1 mole) of cyanuric chloride was added. To this stirred suspension was added 680 grams (3.3 moles) of 4-amino-N-(1,4 dimethylpentyl)aniline dropwise over 1 hour period keeping the temperature between $-10°$ and $-5°$ C. Over 1 hour the reaction mixture was warmed to 30° C. then held for 16 hours at 30° C. The reaction mixture was refluxed for 1 hour at about 80° C. The reaction was followed by high performance liquid chromatography by observing the disappearance of the starting amine, and the conversion of the intermediate mono- and bis- substituted compounds to the final tris-substituted product. After cooling to 60° C. 240 grams (3 moles) of 50 percent sodium hydroxide solution was added dropwise over 1 hour period. The sodium chloride was removed by filtration at 40° C. The filtrate was cooled to 10° C. and the solvent was decanted off. The oily lower layer was extracted with water at 60° C. then crystallized from fresh isopropanol. The title compound was recrystallized from hexane and it melted at 128°–132° C. The yield was 78.1 percent. The infrared spectrum was consistent with the structure. Relative area HPLC analysis of the product showed it to be 95.8 percent pure.

Example 1(A):
Bis(1,3,5-Triazinyl)P-Phenylenediamines

The reaction mass of Example 1 above also contained in small amounts two additional compound, which can be considered to be reaction products of cyanuric chloride with N-(1,4 dimethylpentyl)-p-phenylenediamine. These materials were identified by mass spectroscopy of fractions separated from the reaction by High Performance

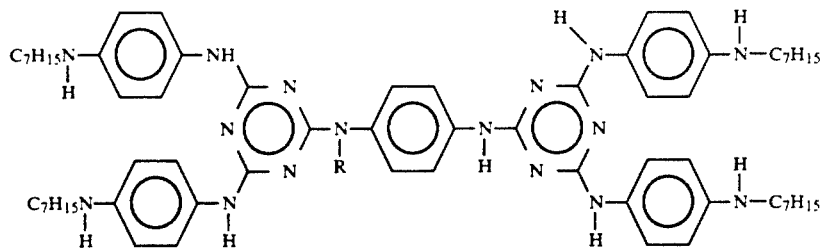

Example 1(A) was determined to have a molecular weight of 1082 and identified as N,N'-bis[4,6-bis(N-1,4-dimethylpentyl-p-phenylenediamino-1,3,5-triazinyl-2]p-phenylenediamine. The R in the foregoing structural formula is hydrogen for this compound.

EXAMPLE 1(B)

Had a molecular weight of 1180 and $R=C_7-H_{15}$ in the foregoing structure. The compound is identified as N-1,4-dimethylpentyl-N,N' bis[4,6-bis(N-1,4-dimethylpentyl-p-phenylenediamino-1,3,5 triazinyl-2)]p-phenylenediamine. The general structure for these bis compounds is believed to be the following:

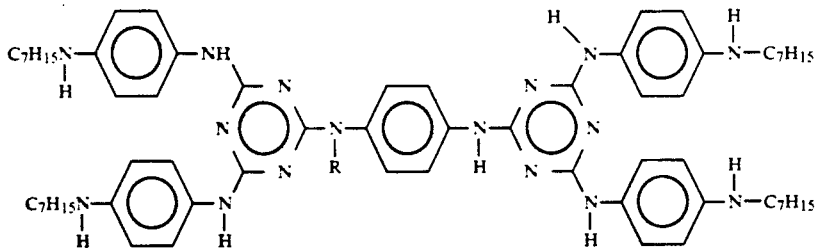

Example 2:
2,4,6-Tris(N-Isopropyl-P-Phenylenediamino)-1,3,5-Triazine

In a 2-liter, four-necked, round-bottomed flask equipped with a thermometer, a mechanical stirrer, a condenser, and a dropping funnel was placed 650 ml. of isopropanol. The isopropanol was cooled to −5° C. and 36.8 grams (0.2 mole) of cyanuric chloride was added. To this stirred suspension was added a solution of 90 grams (0.6 mole) of 4-amino-N-isopropylaniline in 100 ml. of isopropanol dropwise over 1 hour period keeping the temperature between −5° and 0° C. Over ½ hour the reaction mixture was warmed to 30° C. then refluxed for 2 hours. The reaction was followed by high performance liquid chromatography by observing the disappearance of the starting amine, and the conversion of the intermediate mono- and bis-substituted compounds to the final tris-substituted product. The reaction mixture was cooled, and allowed to stand overrnight. The amine hydrochloride salt was neutralized by adding 96 grams (0.6 mole) of 25 percent sodium hydroxide solution over ½ hour period, and then refluxing the mixture for ½ hour. The title compound precipitated upon cooling and was isolated by filtration, washed with isopropanol and hot water (60° C.), M.P. 196°-198° C. The yield was 75.2 percent. The infrared spectrum was consistent with the structure. Relative area HPLC analysis of the product showed it to be 95.3 percent pure.

Example 3:
2,4,6-Tris(N-Cyclohexyl-P-Phenylenediamino)-1,3,5-Triazine

The procedure of Example 2 was repeated except on a 0.1 molar scale with 4-amino-N-cyclohexylaniline used to produce the title compound, M.P. 215°-217° C. The yield was 89.9 percent. The infrared spectrum was consistent with the structure. Relative area HPLC analysis of the product showed it to be 90.1 percent pure.

Example 4:
2,4,6-Tris(N-Sec-Butyl-P-Phenylenediamino)-1,3,5-Triazine

The procedure of Example 2 was repeated except that 4-amino-N-sec-butylaniline was used to produce the title compound, M.P. 167°-169° C. The yield was 90.8 percent. The infrared spectrum was consistent with the structure. Relative area HPLC analysis of the product showed it to be 94.6 percent pure.

Example 5:
2,4,6-Tris(N-1,3-Dimethylbutyl-P-Phenylenediamino)-1,3,5-Triazine In a 3-liter, four-necked, round-bottomed flask equipped with a thermometer, a mechanical stirrer, a condenser, and a powder funnel was placed a solution of 316.8 grams (1.65 moles) of 4-amino-N-(1,3 dimethylbutyl)aniline in 1500 ml of isopropanol. The temperature of the solution was adjusted to 30° C. and 92.2 grams (0.5 mole) of cyanuric chloride was added over ½ hour period keeping the temperature between 30° to 40° C. The reaction mixture was refluxed for 1½ hours. The reaction was followed by high pressure liquid chromatography by observing the disappearance of the starting amine, and the conversion of the intermediate mono- and bis-substituted compounds to the final tris-substituted product. After cooling the reaction mixture to 60° C. 120 grams (1.5 moles) of 50 percent sodium hydroxide solution was added dropwise over 1 hour period. The sodium chloride was removed by filtration at 40° C. The filtrate was charged back to the reaction flask, and 250 ml of water was added dropwise. The title compound precipitated, and was removed by filtration, M.P. 124°-127° C. The yield was 82.6 percent. The infrared spectrum was consistent with the structure. Relative area HPLC analysis of the product showed it to be 95.3 percent pure.

Example 6:
2,4,6-Tris(N-1-Methylheptyl-P-Phenylenediamino)-1,3,5-Triazine

The procedure of Example 5 was repeated except on a 0.225 molar scale with 4-amino-N-(1-methylheptyl)aniline used to produce the title compound. After recrystallization from a 28 percent toluene hexane mixture the melting point of the product was 87°-90° C. The infrared spectrum was consistent with the structure, and the relative area HPLC analysis of the product showed it to be 90.7 percent pure.

Example 7:
2,4,6-Tris(N-2,4-Di-Tert-Butylcyclohexyl-P-Phenylenediamino)-1,3,5-Triazine The procedure of Example 5 was repeated except on a 0.25 molar scale with 4-amino-N-(2,4-di-t-butylcyclohexyl)aniline used to produce the title compound, M.P. 147°-152° C. The yield was 85.7 percent. The infrared spectrum was consistent with the structure.

Example 8:
2,4,6-Tris(N-2-Sec-Butylcyclohexyl-P-Phenylenediamino)-1,3,5-Triazine The procedure of Example 5 was repeated except on a 0.25 molar scale with 4-amino-N-(2-sec-butylcyclohexyl)aniline used to produce the title compound. The product didn't crystallize, and was isolated as a pot residue, M.P. 122°-130° C. The yield was 95.8 percent. The infrared spectrum was consistent with the structure, and the relative area HPLC analysis of the product showed it to be 86.6 percent pure.

Example 9:
2,4,6-Tris(N-1,4-Dimethylpentyl-2-Methyl-P-Phenylenediamino)1,3,5-Triazine In a 1-liter, four-necked, round-bottomed flask equipped with a thermometer, a mechanical stirrer and a condenser was placed a solution of 176 grams (0.80 mole) of 4-amino-N-(1,4-dimethylpentyl)-2-methylaniline in 500 ml of isopropanol. The temperature of the solution was adjusted to 25° C. and 36.8 grams (0.20 mole) of cyanuric chloride was added over a 15 minute period at 25° C. The reaction mixture was held for 15 minutes at 25° C., then refluxed for two hours. The reaction was followed by high performance liquid chromatography by observing the disappearance of the starting amine and the conversion of the intermediate mono- and bis-substituted compounds to the final tris-substituted product. The reaction mixture was cooled to 25° C. and the trihydrochloride of the title compound was removed by filtration. The trihydrochloride was charged back to the reaction flask and 500 ml of isopropanol was added. The temperature was adjusted to 60° C., 96.0 grams (0.60 mole) of 25% sodium hydroxide solution was added. Upon cooling of the isopropanol layer the title compound oils out. It was extracted three times with 20 percent aqueous isopropanol and vacuum stripped to dryness. It melted at 70°-73° C. The yield was 57.8 percent. The infrared spectrum was consistent with the structure. Relative area HPLC analysis of the product showed it to be 94.7 percent pure.

Example 10:
2,4,6-tris(N-1,4-dimethylpentyl-2-ethyl-p-phenylenediamino)-1,3,5-triazine The procedure of Example 9 was repeated, except 4-amino-N-(1,4-dimethylpentyl)-2-ethyl aniline was used to produce the title compound, m.p. 79°-83° C. The yield was 97.2 percent. The infrared spectrum was consistent with the structure. Relative area HPLC analysis of the product showed it to be 93.6 percent pure.

Example 11:
2,4,6-tris(N-isopropyl-2-ethyl-p-phenylenediamino)-1,3,5-triazine In a 1-liter, four-necked, round-bottomed flask equipped with a thermometer, a mechanical stirrer and a condenser was placed a solution of 122.4 grams (0.66 mole) of 4-amino-N-(isopropyl)2 ethylaniline in 300 ml of isopropanol. The temperature of the solution was adjusted to 10° C. and 36.8 grams (0.20 mole) of cyanuric chloride was added over a ½ hour period at 15° C. The reaction mixture was refluxed for two hours. The reaction was followed by high pressure liquid chromatography by observing the disappearance of the starting amine and the conversion of the intermediate mono- and bis-substituted compounds to the final tris-substituted product. After cooling to 60° C., 120 grams (0.60 mole) of 20 percent sodium hydroxide solution was added dropwise over a ½ hour period. The water layer was removed and discarded. The title compound precipitated upon cooling and was isolated by filtration and washed with aqueous isopropanol. It was recrystallized from isopropanol. It melted at 173°-175° C. The yield was 94.4 percent. The infrared spectrum was consistent with the structure. Relative area HPLC analysis of the product showed it to be 96.3 percent pure.

Example 12:
2,4,6-tris(N-isopropyl-2-methyl-p-phenylenediamino)-1,3,5-triazine The procedure of Example 11 was repeated, expect 4-amino-N-(isopropyl)-2-methylaniline was used to produce the title compound, m.p. 185°-186° C. The yield was 82.3 percent. The infrared spectrum was consistent with the structure. Relative area HPLC analysis of the product showed it to be 92.7 percent pure.

Example 13:
2,4,6-tris[N,N'-bis(isopropyl)-p-phenylenediamino]-1,3,5-triazine In a 1-liter, four-necked, round-bottomed flask equipped with a thermometer, a mechanical stirrer and a condenser was placed a solution of 99 grams (0.515 mole) of N,N'-bis-(isopropyl)-p-phenylenediamine in 100 ml of toluene. The temperature of the solution was adjusted to 25° C. and 30.7 grams (0.17 mole) of cyanuric chloride was added as the reaction mixture exothermed to 60° C. The reaction mixture was refluxed for three hours. The reaction was followed by high performance liquid chromatography by observing the disappearance of the starting amine and the conversion of the intermediate mono- and bis-substituted compounds to the final tris-substituted product. The reaction mixture was cooled to 80° C. and 140 grams (0.50 mole) of 14.3 percent sodium hydroxide solution was added. After refluxing for one hour the water layer was removed. The toluene layer was stripped. The residue was taken up in hexane and a small amount of insoluble material was removed by filtration. The filtrate was stripped and the title compound was isolated as a pot residue, m.p. 156°-170° C. The yield was 74.3 percent. The infrared spectrum was consistent with the structure and the relative area HPLC analysis of the product showed it to be 77.8 percent pure.

Example 14:
2,4,6-tris[N,N'-bis-1,4-(dimethylpentyl)-p-phenylenediamino]-1,3,5-triazine The procedure of Example 13 was repeated, except N,N'-bis(1,4-dimethylpentyl)-p-phenylenediamine was used to produce the title compound. The product was isolated as an oily pot residue. The yield was 97.9 percent. The infrared spectrum was consistent with the structure and the relative area HPLC analysis of the produced showed it to be 67.1 percent pure.

Example 15:
2,4,6-Tris(N'-2-Isopropylphenyl-P-Phenylenediamino)-1,3,5-Triazine In a 1-liter, four-necked, round-bottomed flask equipped with a thermometer, a mechanical stirrer and a condenser was placed a solution of 58.8 grams (0.26 mole) p-amino-2-isopropyldiphenylamine in 177 grams of isopropanol. The temperature of the solution was adjusted to 15° C. and 14.7 grams (0.08 mole) of cyanuric chloride was added over a ½ hour period as the reaction temperature rose to 25° C., then heated to 75° C., and held for five hours. The reaction was followed by high performance liquid chromatography by observing the disappearance of the starting amine and the conversion of the intermediate mono- and bis-substituted compounds to the final tris-substituted product. The reaction mixture was cooled to 20° C. and the trihydrochloride was neutralized with a dilute sodium hydroxide solution. After cooling to 25° C. the water layer was removed. The isopropanol layer was stripped. The residue was removed by filtration. The filtrate was stripped and the title compound was isolated as a pot residue. It melted at 85° C. The yield was 57.6 percent. Relative area HPLC analysis of the product showd it to be 73 percent pure.

Example 16:
2,4,6-Tris(N'-2-Isopropylphenyl-3-Isopropyl-P-Phenylenediamino)-1,3,5-Triazine In a 1-liter, four-necked, round-bottomed flask equipped with a thermometer, a mechanical stirrer and a condenser was placed a solution of 69.7 grams (0.26 mole) of 4-amino-2,2'-diisopropyldiphenylamine in 209.1 grams of isopropanol. The temperature of the solution was adjusted to 150° C. and 14.7 grams (0.08 mole) of cyanuric chloride was added over a ½ hour period as the reaction temperature rose to 25° C. After holding the reaction mixture for one hour at 25° C., the reaction temperature was adjusted to 75° C. and held for seven hours. During this period a solution of 20 grams of water in 50 grams of isopropanol was added to dissolve the trihydrochloride precipitate. The reaction was followed by high performance liquid chromatography by observing the disappearance of the starting amine and the conversion of the intermediate mono- and bis-substituted compounds to the final tris-substituted product. A solution of 19.9 grams (0.249 mole) of 50 percent sodium hydroxide in 83 grams of water was added and the reaction temperature raised to 82° C. for one hour. The title compound precipitated upon cooling and was isolated by filtration and triturated in hexane. It melted at 85° C. The yield was 73 percent and relative area HPLC analysis showed it to be 87 percent pure.

Example 17:
2-(N-1,4Dimethylpentyl-P-Phenylenediamino)-4,6-Bis-Mercapto-1,3,5-Triazine Into a 2-liter, three-necked, round-bottomed flask equipped with a mechanical stirrer, a thermometer and an addition funnel was placed 46.1 grams (0.25 mole) of cyanuric chloride and 400 ml of acetone. The resulting solution was cooled to −8° C. (ice/acetone). A solution containing 53.6 grams (0.26 mole) of 4-amino(N-1,4-dimethylpentyl)aniline and 200 ml of acetone was added dropwise, via addition funnel, to the cold cyanuric chloride solution over a 45 minute period. The temperature of the reaction solution was maintained at −5° C. throughout the addition, and it was allowed to rise to 26° C. after the addition was complete. The amine hydrochloride was then neutralized with the addition of an aqueous sodium carbonate solution (13.3 grams, 0.13 mole, in 100 ml of water).

In a second two-liter flask, equipped similarly as above, was placed 66.3 grams (0.51 mole) of 60 percent sodium sulfide and 200 ml of water. The substituted triazine solution was transferred into an addition funnel and, subsequently, was added dropwise to the rapidly stirring sodium sulfide solution. The temperature of the solution remained at 26° C. during the 20 minute addition period. The resulting solution, having a pH of 13.4, was neutralized to pH 7.0 with a dilute HCl solution. The solvent was then removed at reduced pressure, yielding a dark residue. This residue was extracted with 300 ml and 100 ml of methylene chloride; the extracts were combined and dried over sodium sulfate. The solution was filtered and crystallization of the product was effected by the addition of hexane to the filtrate. The total yield for three crystallization crops was 92.0 percent (m.p. 201°–205° C.). Relative area by HPLC analysis indicates a product purity of 93.2 percent, assuming a mixture of thione and thiol tautomers. Infrared spectra of the product are consistent with the proposed structures.

Example 18:
1,6-Bis(2-Imino-4,6-Dichloro-1,3,5-Triazino) Hexane

In a 1-liter, four-necked, round-bottomed flask equipped with a thermometer, a mechanical stirrer and a condenser was placed a solution of 92.0 grams (0.50 mole) of cyanuric chloride in 500 ml of acetone. The temperature of the solution was adjusted to 0° C. and a solution of 29.0 grams (0.25 mole) of 1,6-hexanediamine in 100 ml of water was added over a one hour period at 0° to 5° C. The reaction mixture was held for 15 minutes at 0° C., then 40.0 grams (0.50 mole) of 50 percent sodium hydroxide solution was added over a 15 minute period. The title compound was isolated by filtration and washed with water. It was recrystallized from toluene. It melted at 189°–191° C. The yield was 73.8 percent. The infrared spectrum was consistent with the structure. Relative area HPLC analysis of the product showed it to be 95.3 percent pure.

Example 19:
1,6-Bis[2-Imino-4,6-Bis(N-1,4-Dimethylpentyl-P-Phenylenediamino)-1,3,5-Triazino] hexane In a 1-liter, four-necked, round-bottomed flask equipped with a thermometer, a mechanical stirrer and a condenser was placed a solution of 20.6 grams (0.05 mole) of 1,6-bis(2-imino-4,6,-dichloro-1,3,5-triazino)-hexane (from Example 18) and 200 ml of toluene. To this stirred suspension was added 45.3 grams (0.22 mole) of 4-amino-N-(1,4-dimethylpentyl)aniline as the reaction temperature was allowed to exotherm to 55° C., then refluxed for two hours. The reaction was followed by high performance liquid chromatography by observing the disappearance of the starting amine and the conversion of the intermediate mono-, bis-, and tris-substituted compounds to the final tetrakis-substituted product. After adding 66 grams (0.20 mole of 12.2 percent sodium hydroxide solution the reaction was refluxed an additional ½ hour. After the addition of 100 ml of toluene the water layer was removed. The toluene layer was extracted with water. The title compound was precipitated by the addition of 500 ml of hexane. It was isolated by filtration and recrystallization from isopropanol. It melted at 88°–93° C. The yield was 88.1 percent. The infrared spectrum was consistent with the structure. Relative area HPLC analysis showed it to be 92.6 percent pure.

Example 20:
1,6-Bis[2-Imino-4,6-Bis(N-Phenyl-P-Phenylenediamino)-1,3,5-Triazino]Hexane The procedure of Example 19 was repeated, except 4-aminodiphenylamine was used to produce the title compound, m.p. 127°–132° C. The yield was 88 percent. The infrared spectrum was consistent with the structure. Relative area HPLC analysis of the product showed it to be 87.8 percent.

Antiozonant Utility Examples 21-36

The N-alkylarylenediamino triazine compounds of the invention function as outstanding antiozonants in rubber polymers with no migratory staining tendency evident at this time. The following examples demonstrate their utility in a variety of ozone and color stability test regimes. All tests utilize the triazines in vulcanized rubber compounds as are typical in the industry. The following test formulations I and II are typical rubber compounds.

| TEST FORMULATION | Parts by Weight | |
|---|---|---|
| | I | II |
| Natural Rubber (SMR5CV) | 50.0 | 60.0 |
| Polybutadiene (cis 1,4 BR) | 50.0 | 40.0 |
| Carbon Black (N-326) | 50.0 | 47.5 |
| Zinc Oxide | 3.0 | 3.5 |
| Microcrystalline Wax | 1.5 | 3.5 |
| Stearic Acid | 1.0 | 1.5 |
| Aromatic Oil | 5.0 | — |
| Naphthenic Oil | — | 12.0 |
| Benzothiozole Sulfenamide | 1.0 | 1.0 |
| Sulfur | 2.0 | 1.75 |
| Antiozonant - Variable | Variable | Variable |

Table of Antiozonants

Comparative A—N-phenyl-N'-(1,3-dimethylbutyl)-p-phenylenediamine (commercially available as Flexzone TM 7F from Uniroyal Chemical Company)

Comparative B—mixed diaryl-p-phenylenediamine (commercially available as Novazone TM AS from Uniroyal Chemical Company)

Example 1-2,4,6-tris(N-1,4-dimethylpentyl-p-phenylenediamino)-1,3,5-triazine

The foregoing test formulations were used for all test samples unless otherwise noted. The formulations are an approximation of typical tire sidewall compounds. The identity and level of the antiozonant are the variables to be evaluated in the subsequent examples.

The test formulations were utilized to make uncured test sheets by preblending the natural rubber and polybutadiene. Once blending was accomplished, all other ingredients except the sulfur and benzothiazole sulfenamide were added to form a nonproductive compound and in a subsequent mixing step, the foregoing ingredients were added. Tests sheets for the subsequent testing were cured in a platen press between heated plates for a time sufficient to achieve full cure. For the purposes of testing, a fifteen minute cure at 160° C. was normally utilized. The exact sample configuration of the test specimens for the ozone testing varies by the description of the ASTM method utilized. Reference is made to the ASTM test methods and such methods are incorporated herein by reference to abbreviate the required descriptive information regarding specimen preparation, test methods and test results.

Ozone Test Results

Ozone testing was conducted utilizing the standard test method of ASTM D1149-81 which is titled Rubber Deterioration—Surface Zone Cracking in a Chamber (Flat Specimen). This method covers the estimation of the resistance of vulcanized rubber to cracking when exposed to an atmosphere containing ozone. Rubber specimens are kept under a surface tensile strain and the ozone content in the test chamber is maintained at a 50 part per hundred million level in a 100° F. (38° C.) test chamber. A common designation for this test is the bent loop test method since the test specimen is placed under strain by having it clamped in a looped configuration in which varying degrees of strain and elongation result. This bent loop configuration is an extremely severe test configuration in which failure can be expected in a relatively few hours given the high temperature and high ozone atmosphere in which the test samples are placed.

TABLE I

STATIC OZONE TESTING
(Results in Hours)

| ANTIOZONANT, 4 PHR | Blank | Comparative A | Example 1 |
|---|---|---|---|
| EXAMPLE # | 20 | 21 | 22 |
| OZONE BOX - STATIC TEST | | | |
| Unaged | | | |
| No Cracks | — | — | 1128 |
| Cracked | 6 | 600 | — |
| 6 Months Aged | | | |
| No Cracks | — | — | 1080 |
| Cracked | 8 | 24 | — |
| 12 Month Aged | | | |
| No Cracks | — | — | 1040 |
| Cracked | 17 | 40 | — |

The prepared test formulation I specimens were aged unstressed at room temperature at six months and twelve months and tested. Accordingly, three sets of test data are presented: unaged, six month and twelve month aged. The Example 20 column headed by the term blank denotes a formulation which contains no antiozonant protection. That unprotected sample broke in between six and seventeen hours of exposure depending upon the degree of aging which the specimen underwent prior to ozone exposure. Example 21 with Comparative A is the result of the conventional paraphenylenediamine (Flexzone 7F) added at four parts PHR and it cracked between 600 and as low as 24 hours of exposure. In Example 22, the rubber formulation protected by the substituted triazine of the invention shown in Example 1 survived between 1040 and 1128 hours for the various unaged and aged samples. It is clear from these results that the ozone protection afforded by the compounds of this invention are outstanding compared to the conventional antiozonants which are well known in the rubber field.

Table II shows the data for static ozone testing conducted in a similar manner to the testing shown in Table I. Test formulation I specimens dumbells, 3 mm by 50 mm were stretched 20% on specially designed racks and the degree of cracking was periodically recorded. Under this method, the test sample is subjected to the ozone atmosphere of 50 parts per hundred million at 100° F. while under 20% elongation or extension. This additional degree of strain is a added characteristic of the sample preparation that is different than the test conducted as shown in Table I. All other details with respect to the test method are similar to those previously reported for the Table I results.

TABLE II

OZONE EXPOSURE 20% EXTENSION
(Results in Hours)

| ANTIOZONANT, 4 PHR | BLANK | COMPARATIVE A | EXAMPLE 1 |
|---|---|---|---|
| EXAMPLE # | 23 | 24 | 25 |

Unaged

TABLE II-continued

OZONE EXPOSURE 20% EXTENSION
(Results in Hours)

| ANTIOZONANT. 4 PHR EXAMPLE # | BLANK 23 | COMPARATIVE A 24 | EXAMPLE 1 25 |
|---|---|---|---|
| No Cracks | — | 600* | 1128 |
| Cracked | 552 | — | |
| 6 Months Aged | | | |
| No Cracks | — | — | 1080 |
| Cracked | 8 | 24 | |
| 12 Month Aged | | | |
| No Cracks | — | — | 1040 |
| Cracked | 12 | 56 | — |

*Very slight cracking is visible

The unprotected blank test specimens of Example 23 survived between 12 and 552 hours depending on how long the sample was aged. The Comparative A composition when in an unaged condition at 600 hours showed very slight cracking. The six month and twelve month aged Example 24 showed cracking of the sample in between 56 and 24 hours. The compounds of this invention shown as Example #25 again showed very dramatic improvements over the prior art antiozonant in providing protection which exceeded 1000 hours at these test conditions. This again demonstrates the superiority of the substituted triazines of this invention over the conventionally used antiozonant of the paraphenylenediamine class.

Rubber articles must be protected against ozone when they are subjected to such exposure on outdoor weathering. One of the most difficult applications is on a tire where the vehicle remains out of doors and in ozone bearing atmosphere for an indefinite period of time. The true service conditions under which tires operate are not well duplicated by either static ozone tests such as those described in Table I and II nor are they well duplicated using dynamic test procedures such as DeMattia Flex Testing. In an effort to simulate a typical tire surface condition the following test method is utilized. In the testing scheme, samples are mounted in southern facing test fixtures outdoors, exposed to the full outdoor environmental conditions as are present in Naugatuck, Conn. The samples are continuously flexed for 8 hours over approximately a 78° angle. After this flexing period the sample is then relaxed and remains in that relaxed, static condition for 16 hours. This protocol is repeated day after day until the deterioration as evidenced by the appearance and growth of cracks on the sample surface is observed and recorded. This intermittent flex/relaxation test is felt to correlate well with the actual conditions under which a tire operates. That is, the tire is driven for a number of hours in which it is cycled to similar extensions as are accomplished during the flexing portion of the test. Then the tire sits for a prolonged period of time in a static condition which is reproduced in the 16 hour static portion of the cycle. The test results are expressed in kilocycles. During the flexing portion of the test, the samples are flexed through a 78° angle at about 8.5 kilocycles per hour.

TABLE III

DYNAMIC OZONE TESTING
(Results in Kilocycles)

| ANTIOZONANT. 4 PHR EXAMPLE # | Blank 26 | Comparative A 27 | Example 1 28 |
|---|---|---|---|
| 8 HOUR FLEX/16 HOUR STATIC RESULTS IN KILOCYCLES | | | |
| Unaged | | | |
| No Cracks | — | — | 8584 |
| Cracked | 1694 | 8264 | |
| ¹6 Months Aged | | | |
| No Cracks | — | 13896* | 16588* |
| Cracked | 2969 | — | — |
| ¹12 Month Aged | | | |
| No Crack | — | 7655* | 7655* |
| Cracked | 1165 | | |

¹Test ongoing
*Very, very slight cracking is visible

This dynamic flexing test uses rectangular specimens 12 mm by 76 mm with a 3 mm radius circular groove across the center of the specimen.

It is apparent from the results, that Example 26 which contained no antiozonant survived less than 3000 kilocycles under this test. Examples 27 and 28, which are protected by the paraphenylenediamine of the prior art and a triazine of this invention, respectively, exhibited very significant improvements in the ability to withstand the outdoor aging. The triazine compound of the invention protected the sample of Example 28 with very nearly the same result as the paraphenylenediamine of Comparative A, which is generally considered to be one of the best antiozonants available for dynamic applicants.

ANTIOZONANT BLENDING—EXAMPLES 29-32

The triazine compounds of the invention, when compared to N-phenyl-N'-(1,3-dimethylbutyl)-p-phenylenediamine (Comparative A-Flexzone 7F) generally exhibit much better protection under static conditions and slightly poorer protection under severe dynamic conditions as judged by various laboratory test methods. However, it has been quite unexpectedly and surprisingly found that the dynamic protection properties may be greatly improved by blending the triazine compounds with conventional p-phenylene diamines. This is accomplished without sacrificing static condition ozone protection. Examples 29-32 below demonstrate this synergistic effect.

In Examples 29 and 30, the antiozonant of Example 1 was blended with two conventional antiozonants to evaluate the cumulative effect under both static and dynamic ozone testing conditions. The results were compared to unblended controls 30 and 31. The rubber formulation utilized was the same as the Test Formulation I previously used except that the microcrystalline wax was deleted to assure that the antiozonant effect of the wax was not present to affect the results.

The Outdoor Dynamic Ozone test was conducted in a similar manner to the 8 hour flex/16 hour static test for Examples 26-28 of Table III except that the flexing at 8.5 kilocycles per hour is run continuously. There is no relaxation period. The test was ongoing, and therefore, no samples have yet reached the point of final cracking (failure).

The Ozone Box Static Test was run as described for Examples 20-22.

TABLE IV

| | ANTIOZONANT BLEND TESTING | | | |
|---|---|---|---|---|
| EXAMPLE # | 29 | 30 | 31 | 32 |
| | ANTIOZONANT, PHR | | | |
| Example 1 | 2.5 | 3.0 | — | 4.0 |
| Comparative A | — | 1.0 | 4.0 | — |
| Comparative B | 1.5 | — | — | — |
| | OZONE BOX STATIC TEST (in hours) | | | |
| No Cracks | 1016 | 1016 | — | 1016 |
| *VVS | — | — | — | — |
| Cracked | — | — | 216 | — |
| | OUTDOOR DYNAMIC TEST Continuous Flexing (in kilocycles) | | | |
| No Cracks | 14583** | 14583** | 14583** | — |
| *VVS | — | — | — | 4231 |
| Cracked | — | — | — | — |

*VVS - First appearance of very, very slight cracks
**Test still underway last reading at 14583 kilocycles The results shown in Table IV for the Ozone Box Static Test show that Comparative A (Flexzone 7F) cracks after 216 hours (Example 31) while the compound of Example 1, used in Examples 29, 30, 32 alone or in combination with Comparative A or B afforded excellent protection as indicated by the fact that no cracks were evident after 1016 hours.

The Outdoor Dynamic Test results of Examples 29-31 show that the blends of Example 1 with Comparative A and B showed excellent protection under dynamic conditions. The blends of Examples 29 and 30 unexpectedly improved the Dynamic Ozone resistance compared to Example 32 which used the compound of Example 1 alone.

NON-STAINING CHARACTERISTICS—EXAMPLES 33-35

Samples specimens were prepared using the test formulation I set forth previously but without wax. The test formulation was compounded, mixed and cured into flat test sheets for subsequent analysis of discoloration and staining characteristics. The specific testing was conducted in accordance ASTM-D925-83 Method C. The Method C judges the degree of staining tendency of material by determining the amount of discoloration that occurs from the substrate material through a white lacquer coating which has been placed on the test sample. The test formulation previously set forth for all test samples of the invention was utilized. Once the test specimen was mixed and cured, it was coated with a veneer of white lacquer in accordance with the ASTM-D925 procedure. It was then exposed to a sunlamp light source in a suitable test chamber for a specified period of time. The Hunter Lab TM Colorimeter test apparatus was utilized to objectively determine the change in the color of the white lacquer during the four-hour exposure to the sun lamp. ASTM D2244-79 titled "Color Differences of Opaque Materials", reports a number of characteristics by the standard difference letters a, b, and L. Since the staining characteristics of normal antiozonants are very extreme, the L color scale is reported below. The L color scale is a scale from 0 to 100 with a 0 value being totally black and a 100 value being pure white. Therefore the higher the L value, the whiter the sample. The Test formulation of Example 33 was prepared as a blank which contain no antiozonant. Example 35 contains the antiozonant of the invention described in Example 1, 2,4,6-tris(N-1,4-dimethylpentyl-p-phenylenediamino)-1,3,5-triazine.

Example 34 uses the Comparative A material which is N-phenyl-N'-(1,3-dimethylbutyl)-p-phenylenediamine (Flexzone 7F, available from Uniroyal Chemical Company, Inc.). The test results of the three samples are presented below in Table V showing the Hunter "L" value after four hours of exposure.

TABLE V

| HUNTER "L" COLOR RESULTS | | | |
|---|---|---|---|
| EXAMPLE | 33 | 34 | 35 |
| ANTIOZONANT | blank | Comparative A | Example 1 |
| | 87.9 | 32.6 | 81.5 |

The results shown above clearly show that the conventional paraphenylenediamine material of Example 34 shows significant staining (32.6) after 4 hours of exposure. But by contrast the test formula containing the compound of the invention of Example 1 had a color value of 81.5 which is very close to 87.9 value reported for the blank of Example 33. Thus, the compound of the invention is shown to have minimal diffusion staining which is an extremely unusual result for stabilizer of the amine class. Thus, the compounds of the invention can be advantageously utilized as antiozonants without the normal accompanying problems of diffusion staining and severe discoloration such as that shown in Comparative A results above. This class of materials could be described as non-staining antiozonants.

The intermittent flex/relaxation test of Table III above was repeated on test specimens of formulation I containing 4 PHR of compounds of Examples 13, 14, 19 and 20. Again, the results are compared to a blank, Example 26, which contained no antiozonant. It can be seen from Table VI that good to excellent improvement in the ability to withstand the outdoor aging was obtained.

TABLE VI

| DYNAMIC OZONE TESTING (Results in Kilocycles) | | | | | |
|---|---|---|---|---|---|
| ANTIOZONANT, 4 PHR | Blank | Ex. 13 | Ex. 14 | Ex. 19 | Ex. 20 |
| EXAMPLE No. | 26 | 36 | 37 | 38 | 39 |
| 8 HOUR FLEX/16 HOUR STATIC | | | | | |
| Unaged | | | | | |
| No. Cracks | — | — | — | — | — |
| Cracked | 1694 | 1830 | 10837 | 2311 | 1830 |
| 6 Months Aged (Shelf at R.T.) | | | | | |
| No. Cracks | — | — | — | — | — |
| Cracked | 2969 | 6756 | 11150 | 5859 | 5859 |
| 12 Months Aged (Shelf at R.T.) | | | | | |
| No. Cracks | — | — | — | — | — |
| Cracked | 1165 | 3171 | 4547 | 2279 | 1583 |

Example 13, 14, 19 and 20 of Table VII represent outdoor Dynamic Ozone testing conducted in a similar manner to the 8 hour flexing/16 hour static text for Examples 13, 14, 19 and 20 of Table VI, except that the flexing at 8.5 kilocycles per hour is run continuously. There is no relaxation period. Again, good to excellent improvement is shown by the compounds of the invention over that of the blank, Example 4, which contained no antiozonant.

TABLE VII

DYNAMIC OZONE TESTING
(Results in Kilocycles)

| ANTOZONANT, 4 PHR | Blank | Ex. 13 | Ex. 14 | Ex. 19 | Ex. 20 |
|---|---|---|---|---|---|
| EXAMPLE No. | 40 | 41 | 42 | 43 | 44 |
| 8 HOUR FLEX/16 HOUR STATIC | | | | | |
| Unaged | | | | | |
| No. Cracks | — | — | — | — | — |
| Cracked | 3671 | 7572 | 12180 | 8610 | 5769 |
| 6 Months Aged (Shelf at R.T.) | | | | | |
| No. Cracks | — | — | — | — | — |
| Cracked | 5709 | 8782 | 19963 | 8782 | 6436 |
| 12 Months Aged (Shelf at R.T.) | | | | | |
| No. Cracks | — | — | — | — | — |
| Cracked | 3152 | 6203 | 8749 | 6203 | 4421 |

Compounds of Examples 13, 14, 19 and 20 were subjected to an outdoor static, bent loop test similar to the Static Ozone testing of Table I, except that the test was conducted outdoors and the results are reported in days instead of hours. The test is ongoing except for Example 19. The current status of the test appears in Table VIII.

TABLE VIII

DYNAMIC OZONE TESTING
(Results in Days)

| ANTOZONANT, 4 PHR | Blank | Ex. 13 | Ex. 14 | Ex. 19 | Ex. 20 |
|---|---|---|---|---|---|
| EXAMPLE No. | 45 | 46 | 47 | 48 | 49 |
| OUTDOOR STATIC TEST, BENT LOOP | | | | | |
| Unaged | | | | | |
| No. Cracks | — | — | — | — | — |
| Cracked | 28 | 58 | 146 | 37 | 37 |
| 6 Months Aged (Shelf at R.T.) | | | | | |
| No. Cracks | — | — | — | — | — |
| VS* | 203 | 249** | — | — | 249** |
| Cracked | — | — | — | 153 | — |

*VS - Very slight cracks
**Test still underway, last reading 249 days

Ozone testing was conducted utilizing the standard test method of ASTM D1149-81 described above on test specimens of formulation II containing 3.5 PHR of compounds of Examples 13 and 14.

The test was conducted in a similar manner to the testing shown in Table I. Again, these results are compared to a blank, Example 50, which contains no antiozonant. Clearly, from the results shown in Table IX, the compounds of the instant invention offer excellent ozone resistance.

TABLE VIII

DYNAMIC OZONE TESTING
(Results in Hours)

| EXAMPLE No. | 50 | 51 | 52 |
|---|---|---|---|
| ANTIOZONANT, 3.5 PHR | Blank | Exa. 13 | Ex. 14 |
| OZONE BOX - STATIC TEST | | | |
| Unaged | | | |
| No Cracks | — | 1008 | — |
| Cracked | 48 | * | 768 |
| 6 Months Aged, shelf, R.T. | | | |
| No Cracks | — | — | — |
| Cracked | 8 | 505 | 841 |

*Test still underway, last reading 1008 hours.

Table X shows the data for static ozone testing conducted in a similar manner to the testing shown in Table IX. Test formulation II specimens dumbells were stretched 20% and the testing procedure was the same as used on Table II examples.

The unprotected blank test specimens of Example 50 survived between 8 and 24 hours depending on how long the sample was aged. The unaged and six month aged Examples 13 and 14 showed excellent improvement over the blank.

TABLE X

DYNAMIC OZONE TESTING
(Results in Hours)

| EXAMPLE No. | 52 | 53 | 54 |
|---|---|---|---|
| ANTIOZONANT, 3.5 PHR | Blank | Ex. 13 | Ex. 14 |
| OZONE BOX - STATIC TEST | | | |
| Unaged | | | |
| No Cracks | — | — | — |
| Cracked | 24 | 768 | 144 |
| 6 Months Aged, shelf, R.T. | | | |
| No Cracks | — | — | — |
| Cracked | 8 | 505 | 385 |

The compounds of the invention may be used to good advantage with antioxidants and antiozonants of the prior art in blends to enhance particular properties. While the substituted triazine compounds of the invention have herein described only as antiozonants, it is clear that the materials may also function as antioxidants for rubber, thus providing protection against oxidative degradation as well as ozone protection. It is noted that when used as an antioxidant, the levels are typically much lower per hundred parts of rubber hydrocarbon than when antiozonant protection is required.

The 2,4,6-tris(N-alkyl-p-phenylenediamino)-1,3,5-triazines can be most advantageously used in a tire as a component of any or all of the thermosetting rubber-containing portions of the tire. These include the tread, sidewall and carcass portions of a truck, passenger or off-road vehicle tire which also contain many different reinforcing layers therein. These components typically contain more than one thermosetting rubber polymer in a blend which must be protected from ozone degration, as well as oxidative attack.

Methods of incorporating these compounds into the tire are conventional and well known. These compounds improve the scorch safety of the rubber stock in which they are incorporated compared to conventional paraphenylenediamines.

Unsaturated polymers may be optionally protected against both oxidative and ozone degradation by blending the triazine compounds of the invention with conventional antioxidants. Many classes of phenolics, amines, etc. function as antioxidants. The Index of Commercial Antioxidants and Antiozonants, 3rd Edition published by The Goodyear Tire and Rubber Company lists materials commonly viewed as materials having antioxidant properties, and is incorporated herein by reference. Representative classes of such antioxidant materials are sterically hindered phenols, alkyl-substituted diphenylamines, aryl-substituted diphenylamines, aralkyl-substituted diphenylamines, naphthylamines, reaction products of a diarylamine and a ketone, mono-phenols, bisphenols, polyphenols, hydroquinone derivatives, and polymerized quinolines. The antioxidant system may contain one or more of these materials.

Optimal levels of addition (PHR) for the antioxidants can be easily determined through routine experimentation and may vary widely depending upon the end use application.

In view of the many changes and modifications that may be made without departing from principles underlying the invention, reference should be made to the appended claims for an understanding of the scope of the protection afforded the invention.

What is claimed is:

1. A compound of the general formula (I):

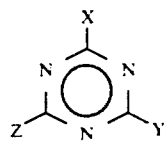

in which
X is

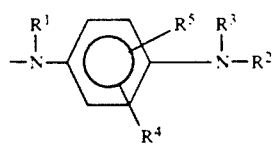

$R^1$ is hydrogen, $C_1$-$C_{11}$ linear or branched alkyl, $C_3$-$C_6$ cycloalkyl, phenyl or phenyl substituted with $C_1$-$C_4$ alkyl;
$R^2$ is

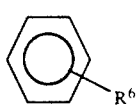

$R^3$ is hydrogen, phenyl or $C_1$-$C_{11}$ linear or branched alkyl;
$R^4$ is hydrogen or $C_1$-$C_8$ linear or branched alkyl;
$R^5$ is hydrogen or $C_1$-$C_8$ linear or branched alkyl;
$R^6$ is $C_1$-$C_8$ linear or branched alkyl or $C_1$-$C_{12}$ alkoxy, hydrogen when $R^1$ is $C_1$-$C_{11}$ linear or branched alkyl or $C_1$-$C_8$ linear or branched alkyl when $R^1$ is hydrogen;
$R^7$ is $C_1$-$C_{12}$ linear or branched alkyl;
Y is, hydrogen, $C_1$-$C_4$ alkyl, —SH, $SR^8$, —OH, —$OR^8$,

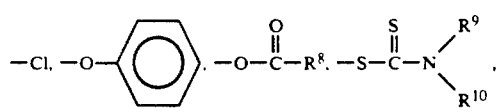

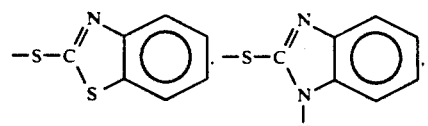

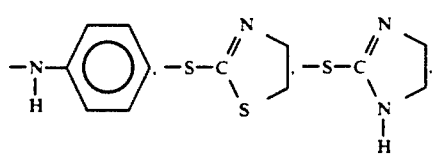

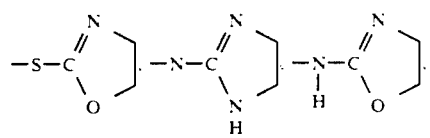

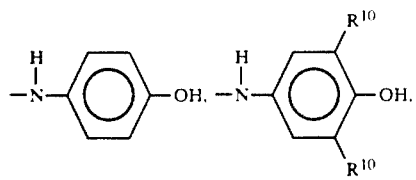

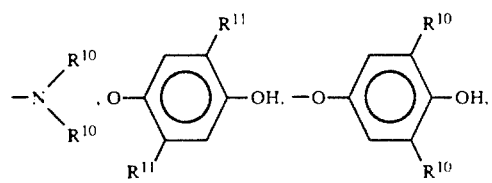

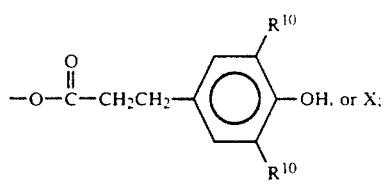

$R^8$ is $C_1$-$C_{12}$ linear or branched alkyl,
$R^9$ is $C_1$-$C_5$ linear or branched alkyl,
$R^{10}$ is $C_1$-$C_5$ linear or branched alkyl,
$R^{11}$ is hydrogen, $C_3$-$C_{16}$ linear or branched alkyl.
Z is X, or Y or

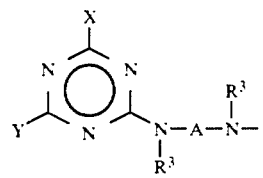

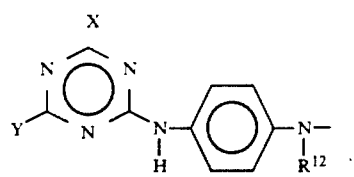

A is $C_2$-$C_{10}$ linear alkylene $C_5$-$C_{10}$ cycloalkylene, phenylene or $C_7$-$C_9$ arylalkylene;
$R^{12}$ is hydrogen or $C_3$-$C_{11}$ alkyl;
when Y and Z are not the same as X, then $R_6$ can be hydrogen;
when Z is the same as Y, then Y may not be —$SR^8$, —OH, —$OR^8$,

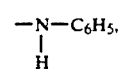

—O—$C_6H_5$.

2. A compound according to claim 1 wherein the $R^2$ or $R^3$ radicals have a secondary carbon atom in the alpha position relative to the nitrogen.

3. A compound according to claim 1 wherein Y and Z are the same and X is different.

4. A compound according to claim 2 selected from 2,4,6-tris(N-1,4 dimethylphentyl-2-ethyl-p-phenylenediamino)1,3,5-triazine; 2,4,6-tris(N-isopropyl-2-ethyl-p-phenylenediamino)1,3,5-triazine; 2,4,6-tris(N-isopropyl-2-methyl-p-phenylenediamino)-1,3,5-triazine, or 2,4,6-tris(N-1,4 dimethylpentyl-2,5-dimethyl-p-phenylenediamino)1,3,5 triazine.

* * * * *